(12) United States Patent
Ross et al.

(10) Patent No.: US 10,345,266 B2
(45) Date of Patent: Jul. 9, 2019

(54) ULTRASONIC NDT INSPECTION SYSTEM

(71) Applicant: INDEPTH INSPECTION TECHNOLOGIES INC, Aurora (CA)

(72) Inventors: Kevin Vincent Ross, Bonnybridge (GB); Arjun Prakash Thattaliyath Kadumberi, Grangemouth (GB); Andrew Lindsay Burns, Dinas Powys (GB)

(73) Assignee: INDEPTH INSPECTION TECHNOLOGIES INC., Aurora (CA)

( * ) Notice: Subject to any disclaimer, the term of this patent is extended or adjusted under 35 U.S.C. 154(b) by 143 days.

(21) Appl. No.: 14/898,510

(22) PCT Filed: Jun. 18, 2014

(86) PCT No.: PCT/GB2014/051872
§ 371 (c)(1),
(2) Date: Dec. 15, 2015

(87) PCT Pub. No.: WO2014/202976
PCT Pub. Date: Dec. 24, 2014

(65) Prior Publication Data
US 2016/0139082 A1    May 19, 2016

(30) Foreign Application Priority Data
Jun. 19, 2013  (GB) .................................. 1310969.9

(51) Int. Cl.
*G01N 29/04* (2006.01)
*G01N 29/06* (2006.01)
(Continued)

(52) U.S. Cl.
CPC .......... *G01N 29/043* (2013.01); *B29C 65/342* (2013.01); *B29C 65/3476* (2013.01);
(Continued)

(58) Field of Classification Search
CPC ........... G01N 29/04; G01N 2291/0235; G01N 2291/044; G01N 2291/2675
(Continued)

(56) References Cited

U.S. PATENT DOCUMENTS 3,414,240 A   12/1968  Jung et al.
3,795,106 A   3/1974   Cherry et al.
(Continued)

FOREIGN PATENT DOCUMENTS

EP     1076597 B1   6/2002
GB     689974 A     4/1953
(Continued)

OTHER PUBLICATIONS

Shin et al, "Nondestructive Testing of Fusion Joints of Polyethylene Piping by Real Time Ultrasonic Imaging;" (NDT Mar. 2005).*
(Continued)

*Primary Examiner* — John E Chapman, Jr.
(74) *Attorney, Agent, or Firm* — Millman IP Inc.

(57) ABSTRACT

A method and system for the ultrasonic non-destructive testing of joints in plastic pipes using A-scans. A hand-held ultrasonic transducer is used to perform an A-scan and a comparison made on a response from the interface region of the joint used to determine a quality of the joint. Levels of result can provide a binary output to give an indication of whether or not a defect is present in the joint. Comparison techniques are described. Tests for coupling efficiency and performance are described making the system useable by an unskilled technician. The system finds application in fault detection on electro-fusion welds in plastic pipe joints.

18 Claims, 1 Drawing Sheet

(51) Int. Cl.
G01N 29/11 (2006.01)
B29C 65/34 (2006.01)
B29C 65/82 (2006.01)
B29C 65/00 (2006.01)

(52) U.S. Cl.
CPC ...... B29C 65/8292 (2013.01); B29C 66/1222 (2013.01); B29C 66/1224 (2013.01); B29C 66/5221 (2013.01); B29C 66/52292 (2013.01); B29C 66/9672 (2013.01); G01N 29/0609 (2013.01); G01N 29/11 (2013.01); B29C 65/3468 (2013.01); B29C 66/71 (2013.01); B29C 66/965 (2013.01); B29C 66/966 (2013.01); G01N 2291/044 (2013.01); G01N 2291/267 (2013.01); G01N 2291/2634 (2013.01); G01N 2291/2675 (2013.01)

(58) Field of Classification Search
USPC .......................................................... 73/588
See application file for complete search history.

(56) References Cited

U.S. PATENT DOCUMENTS

| | | | |
|---|---|---|---|
| 4,132,633 | A | 1/1979 | Saitoh et al. |
| 4,244,531 | A | 1/1981 | Szegvari |
| 5,203,359 | A | 4/1993 | Fesmire et al. |
| 5,234,110 | A | 8/1993 | Kobler |
| 5,370,235 | A | 12/1994 | Stahl et al. |
| 5,894,996 | A | 4/1999 | Williams |
| 6,555,588 | B2 | 4/2003 | Gorski et al. |
| 6,599,950 | B2 | 7/2003 | Jody et al. |
| 6,948,369 | B2 | 9/2005 | Fleming et al. |
| 7,504,535 | B2 | 3/2009 | de Vreede et al. |
| 7,938,007 | B2 | 5/2011 | Huebler et al. |
| 2005/0132809 | A1 | 6/2005 | Fleming et al. |
| 2008/0202333 | A1 | 8/2008 | Matsuura et al. |
| 2009/0114021 | A1 | 5/2009 | den Boer |
| 2009/0277270 | A1 | 11/2009 | Huebler et al. |
| 2010/0031750 | A1 | 2/2010 | Spencer et al. |
| 2012/0032009 | A1 | 2/2012 | Flores |
| 2012/0310551 | A1 | 12/2012 | Na et al. |

FOREIGN PATENT DOCUMENTS

| | | |
|---|---|---|
| GB | 2046909 A | 11/1980 |
| JP | 61233361 | 10/1986 |
| WO | WO 2008/012520 A1 | 1/2008 |

OTHER PUBLICATIONS

Prakash et al., "Ultrasonic Imaging of Electrofusion Welded Polyethylene Pipes Employed in Utilities Industry;" (NDT 2012).*
Hagglund et al., "A Novel Phased Array Ultrasonic Testing (PAUT) System for On-Site Inspection of Welded Joints in Plastic Pipes;" (NDE 2014).*
Qidwai, Uvais et al, "Fuzzy Mapping of Human Heuristics for Defect Classification in Gas Pipelines Using Ultrasonic NDE," IEEE Transactions, 2007.
Prakash, A. et al, "Ultrasonic Imaging of Electrofusion Welded Polyethylene Pipes Employed in Utilities Industry," Centre for Ultrasonic Engineering, Univ of Strathclyde, 2012.
Lutsch, A., "Ultrasonic Reflectoscope With an Indicator of the Degree of Coupling Between Transducer and Object," The Journal of the Acoustical Society of America, Jun. 1958, pp. 544-548; vol. 30, No. 6.
Frielinghaus, R., "Zerstorungsfreie Prufung Von Klebverbindungen Mit Ultraschall," Kunststoffberater, 201975 1, Nov. 1, 1994, pp. 40-45, esp. p. 40 LH col. Fig. 1; p. 41, fig. 5; p. 42, fig. 10; p. 43, RH column.
Wuich, W., "Ultrasonic Testing of Plastics and Bonded Joints," Int'l Polymer Science and Technology, Rapra Technlogy, Shrewsbury, GB, vo. 15, No. 2, Jan. 1, 1988, entire doc.
International Search Report for PCT/GB2014/051872, European Patent Office, dated Oct. 6, 2014, entire document.
GB Search Report for GB1310969.9, Intellectual Property Office of the UK, dated Aug. 12, 2013, entire document.
Hagglund, F. et al, "Development of Inspection Techniques for an Automated NDE Approach for Testing Welded Joints in Plastic PE Pipes," Oct. 26-28, 2011, entire document, presented at AIPnD Conference, Florence, Italy.

* cited by examiner

ULTRASONIC NDT INSPECTION SYSTEM

The present invention relates to a non-destructive ultrasonic inspection system for detecting faults in plastic pipes and in particular, though not exclusively, to an ultrasonic inspection system which uses an A-scan to determine faults in electro-fusion joints in plastic pipes.

The use of plastic materials in industrial pipes is an area of rapid growth. Plastic pipes offer significant advantages over other materials such a metals and concrete for the transportation of fluids as plastic pipes don't corrode, have a longer service life, require replacement less often and are less expensive to install because of their lightness and flexibility. In addition, plastic pipes typically have lower leakage rates due to having an all welded joint system. However, the integrity of plastic pipelines greatly depends on the quality of the welded joints. For example, in the oil and gas industry even a small leakage of gas could lead to an explosion while for the water industry in England and Wales a reported 3.36 billion liters of water a day are lost in leaks. Therefore, it is desirable for both safety and environmental considerations that the rate of failure in such pipes is zero or close to zero.

Two main techniques are used for the welding of plastic pipes: Butt fusion and electro-fusion welding (EFW). Butt fusion joining of plastic pipes requires that the mating surfaces of two pipes are square to each other and properly prepared. The surfaces are simultaneously heated and melted with a hot-plate heater. The hot plate heater is then removed and the melted surfaces are pressed together to form the weld.

In an electro-fusion joint the two pipe segments to be joined are cleaned, scraped and inserted into a polyethylene tubular fitting which has an embedded wire for resistance heating. A current is applied through the wire for a period of time so that the inside of the coupling and the outside of the pipe melt and weld together. The arrangement is then allowed to cool.

These processes are inherently dependent upon the operator and equipment performance to achieve a high quality weld. Defects which typically occur in welds include surface contamination which cause the weld to be polluted; errors in the heating resulting in over heating or insufficient heating, or misalignment of the pipe ends when brought together or when located in the coupling. Consequently non-destructive testing (NDT) of each joint is strongly recommended in addition to joining process control.

Ultrasonic NDT of steel pipes is well established. While A scans are used, which provide a trace of the amplitude of the reflected ultrasound signal against time at a single point, current best practice for inspection of welds in steel pipes relies upon ultrasonic phased array non-destructive evaluation. These B scans give a 2D image of brightness representative of the amplitudes across a volume of the pipe. Colour enhancement may be used to show up the defects more clearly.

In plastics, an ultrasound A-scan has been reportedly tested on a polyethylene (PE) electro-fusion joint: 'An average velocity of the PE was measured as 2.24 Km/s, and attenuation was measured as 3.5 dB/cm and 6 dB/cm at 1 Mhz and 3.5 MHz respectively. With a non-focused 5 MHz traditional normal incident single element transducer and an ultrasonic pulse receiver, PANAMETRICS 5800, it was hard to detect back wall echoes of a PE piping thicker than 2 cm. Also echoes from heating wire was small and the resolution was very poor to tell flaws from heating wires, since the gap between adjacent wires were too small.' Consequently, the very specific acoustic properties of high attenuation and low ultrasonic velocity of plastics have now led researchers to develop ultrasonic test systems using B-scans.

A disadvantage in using B-scan techniques to detect faults in plastics is that the result, which appears as a 2D image of brightness, requires a skilled operator to analyse and interpret. This is particularly the case where an electro-fusion joint is used as the wires will be present in the image. This currently prevents the technique from being operated by pipe laying technicians in the field.

A further disadvantage in using B-scan techniques to detect faults in plastics is in the difficulty in coupling between the phased array probe and the plastic pipe. Non-contact transmission systems, immersion systems or rig arrangements have been the most successful in achieving useful plastic pipe scans. However, these systems are typically limited to a lab-based environment.

There is therefore a need to develop an ultrasonic NDT inspection system for plastics that is operable on site and is rugged. Further the system should be automatic in so far as providing a yes/no answer on fault detection and be simple to operate so that it can be used by a pipe laying technician.

These are the aims of a European (FP7) funded project set-up in 2010 for the development and validation of an automated non-destructive evaluation approach for the inspection of different polyethylene pipe joints in various material grades and pipe sizes.

The fifteen organisations from seven countries considered a number of NDT techniques and decided to develop a phased array ultrasonic inspection system providing B-scans using a water wedge probe. Thus there is a technical prejudice to the use of A-scans to determine faults in plastic pipes.

It is therefore an object of at least one embodiment of the present invention to provide an ultrasonic testing system for use in the non-destructive testing of joints in plastic pipes which uses an A-scan.

According to a first aspect of the invention there is provided a method of non-destructive testing of a joint in plastic pipes, comprising the steps:

a) locating a hand-held ultrasonic transducer at a first point on a first surface of the joint and performing an A-scan through the joint between the first surface and a back surface of the joint at the first point;

b) detecting a trace of the A-scan and identifying an interface response representing one or more reflections of a sound signal from one or more surfaces in a region between the first surface and the back surface;

c) analysing the response by making a comparison to provide a result; and d) outputting the result, the result being indicative of a quality of the joint.

The Applicants have discovered that detailed analysis of the trace of the A-scan is not required and a simple comparison can indicate when a defect is present. It should be noted that the response needs to be from the region between the front and back surfaces and not from either the front or back surfaces.

The interface at the joint will be in the region between the first surface and the back surface and thus defects or flaws at the interface will create a detectable response. This interface response will be different when a defect is present. The Applicants have discovered that for joints that are correctly welded, the plastics fuse and there are less interfaces present to create a reflection, thus the interface response for a defect will be comparatively different enough to provide an indication that a defect is present. By performing an A-scan on a plastic pipe joint, the integrity of the joint may be non-destructively evaluated and the presence of any defect and/or inclusion can be established.

The Applicants have recognised that a useable interface response is better achieved if sufficient sound energy is coupled into the joint.

Preferably the method comprises the step of determining effective coupling is achieved between the joint and the ultrasound transducer. Preferably the step of determining effective coupling is achieved is performed prior to the step of performing an A-scan on the joint. By establishing that effective coupling is in place between the joint and the transducer the output generated by the A-scan can be relied upon to provide an accurate detection.

Preferably, the step of determining effective coupling is achieved comprises detecting a coupling response, representing a reflection of a sound signal from the first surface of the joint, when the sound signal is input at the first point. Effective coupling is achieved when the ring down time of the coupling response is at a minimum. This indicates that a majority of the energy in the sound signal has entered the joint. The method may include the step of notifying a user that effective coupling has been achieved. This may be by a sound or a display, such as a green light. Alternatively, the step of notifying a user may provide a scaled response so that the user is notified as the minimum is approached. Such a scaled response may be in the form of red/amber/green lights or a change in pitch of sound.

The coupling response may be determined from a reflection of a sound signal from an interface in the joint or the back wall. Effective coupling may be determined by measuring the reflected energy or the time taken for a signal to return to the transducer.

The Applicants have also recognised that the quality of the joint can be quantified to provide a level of result, such as a numerical scale.

Preferably, the result is a level on a scale. In this way a numerical scale of, say, 1 to 10 could be used with 1 indicating a very good joint and 10 indicating a very bad joint which has a major defect. In an embodiment, the result is a binary output indicating whether a defect is present or not. The binary output may be in a form which notifies a user of the result, for example, a sound or red light/green light. In this way, a test can be performed by a pipe laying technician.

In an embodiment, the result provides three levels, being indicative of no defects present, definitely a defect present and a possible defect present. This provides a level of confidence in the measurement and depending on the type of joint and its purpose, the user can decide if the joint would pass or fail on a 'possible defect present' result.

Preferably, the step of analysing the response by making a comparison provides a ratio and wherein the ratio is used to determine the level of the result.

The comparison may be to the energy in the sound signal at the transducer. Optionally, the comparison may be to a second trace. The second trace may be a trace of an A-scan performed on a test joint, the test joint being of the same materials and dimensions as the joint and the test joint having no defects. Alternatively, the second trace may be generated from a simulated model of the joint.

Alternatively, the comparison may be to a second response on the trace of the A-scan. In an embodiment the second response is a reflection of the sound signal from the back surface. More preferably, the step of analysing the trace compares a first peak amplitude from the response with a second peak amplitude from the second response to provide the ratio. In this way, a simple analytical model is used to obtain the result as it has been determined that, for a plastic where the back surface has an interface with air, when a typical fault is present the first amplitude peak will be significantly greater than the second amplitude peak.

The comparison may compare the response peak amplitude, pulse width, pulse shape, phase or frequency of the interface response.

The method may comprise the step of performing the A-scan on a butt weld at the plastic pipe joint. Preferably, the method comprises the step of performing the A-scan on an electro-fusion weld at the plastic pipe joint. Whereas the prior art taught away from the use of A-scans as the heating wires could not be identified in the response, the present invention uses the fact that the heating wires will provide an interface response which is less significant in a comparison than a response from a common defect such as a void or grease contamination. When the comparison is made against a trace from a test joint or simulated model, an expected response including the effect of the heating wires will be known, giving greater accuracy to the result.

The method may comprise the step of inputting data relating to the joint. Such data may be the type of plastics, the thickness of the plastic pipes and/or the thickness of the electro-fusion fitting. By inputting this data the step of analysing the interface response can be improved by looking for responses at expected locations on the A-scan trace. Additionally, when the comparison is made against a trace from a test joint or simulated model, the input data will be used to select the stored trace with the best match.

In an embodiment, the step of inputting data relating to the joint can be by scanning a bar code on the plastic pipes and/or the electro-fusion fitting, the bar code containing the data required. In this way, the process of performing a test can be speeded up as a user does not have to manually input the data.

The method may further comprise the step of determining that an A-scan can be performed on the joint. Preferably the step of determining that an A-scan can be performed on the joint is subsequent to the step of determining that effective coupling has been achieved. Preferably the step of determining that an A-scan can be performed on the joint comprises detecting an operating response, representing a reflection of a sound signal from a position after the front surface. This will show that an interface response can be detected. The step may also include determining that the operating response is above a predetermined threshold and/or meets some pre-determined criterion such as having a particular pattern in the time or frequency domain. In this way, a clear interface response will be obtained. The method may include the step of notifying a user that an A-scan can be performed which will indicate that the system is 'ready'. This may be by a sound or a display, such as a green light. By providing a determination that effective coupling has been achieved and that an A-scan can be performed on the plastic a system operator can perform a test and be able to rely on the result of the test.

The coupling response and the operating response may be considered as first and third responses of an A-scan, with the second response being the interface response, and thus the method may comprise performing multiple A-scans at the first point to detect effective coupling, a ready condition and perform a test.

Preferably the method includes repeating the steps at other points on the joint. In this way, an entire weld can be tested on a point by point basis.

According to a second aspect of the invention there is provided an ultrasonic non-destructive testing system for a joint in plastic pipes, the system comprising:

a hand-held ultrasonic transducer, the transducer being located at a first point on a first surface of the joint and operable to perform an A-scan of the joint between the first surface and a back surface of the joint at the first point;

and an operating unit, the operating unit including:

a user interface with one or more inputs for a user to control the system and one or more outputs to display a result of the system; and an analysis module for receiving the A-scan, detecting the presence of an interface response representing a reflection of the sound signal from an interface in a region of the plastic between the first surface and the back surface, performing a comparison and determining the result based on the comparison.

The operating unit may comprise a lap-top, tablet or other hand-held device. The transducer may be located in the operating unit. As the system is hand-held and can be ruggedized, the system can be used in the field at pipe laying sites.

The transducer may be operated from a standard pulser-receiver. This can drive probes within the transducer with the required spectral energy and include sufficient digitisation capabilities at the reception end, for a required dynamic range and bandwidth. In this way, a standard transducer may be used, making the system cheaper to manufacture.

Preferably, the output comprises one or more lights wherein a colour of the light indicates the result. In this way a yes/no result on fault detection can be displayed so that the system is operable by a pipe laying technician.

Preferably the system includes a bar code scanner at the input of the user interface. In this way, information on the joint being tested can be collected and input directly to the analysing module removing the need for a user to type in the information. This speeds up the time to undertake a test and reduces operator errors.

Preferably, the system comprises electronic coupling means to determine effective coupling between the transducer and the first surface of the joint. Electronic coupling means is distinct from mechanical coupling means and preferably uses electronic equipment and software control. Preferably, the coupling means comprises the transducer, the analysis module and the user interface such that a signal from the transducer is input to the joint, a response indicative of coupling is analysed by the analysis module and a result, when effective coupling is achieved, is output on the user interface. In this way, the operator holding the transducer against the joint is given an indication that the transducer and joint are coupled.

Preferably, the system comprises electronic performance means to determine that an A-scan can be performed on the joint. Preferably, the performance means comprises the transducer, the analysis module and the user interface such that a signal from the transducer is input to the joint, a response indicative that the signal has been reflected from position after the front surface is detected by the analysis module and a result, when the response is detected, is output on the user interface. In this way, the operator is notified that the system is ready to perform the test and that a test can be performed. In this way, the system can be used by an unskilled operator.

Preferably, the analytical means is operable to perform a ratio calculation between the interface response and a further response. In an embodiment, the further response is a response from the back surface of the joint. Alternatively, the further response may be a stored response. Preferably, the analysis module includes a data storage facility, there being stored at least one reference A-scan through a joint and wherein the analytical means is operable to compare the A-scan to a stored reference A-scan, the stored reference A-scan including the further response. In an embodiment, further response characteristics are stored and used for the comparison. The further response characteristics may be time domain characteristics like expected peak amplitude; or frequency domain characteristics of the reflection; or a combination of both (such as in wavelets).

Within the scope of this description it will be understood that an A-scan is used to describe an amplitude modulation scan whereby a pulse output from a single element transducer is transmitted into the material being scanned, is reflected from one or more surfaces and then received by the transducer. The pulse is at normal incidence to the material. The received signal can then be displayed as a function of time giving an indication of the depth within the scanned material at which each reflective surface is located. A response is a variation in the trace representing one or more reflections in a region of the scanned material.

Further features are embodied in the description.

In the description that follows, the drawings are not necessarily to scale. Certain features of the invention may be shown exaggerated in scale or in somewhat schematic form, and some details of conventional elements may not be shown in the interest of clarity and conciseness. It is to be fully recognized that the different teachings of the embodiments discussed below may be employed separately or in any suitable combination to produce the desired results.

Accordingly, the drawings and descriptions are to be regarded as illustrative in nature, and not as restrictive. Furthermore, the terminology and phraseology used herein is solely used for descriptive purposes and should not be construed as limiting in scope. Language such as "including," "comprising," "having," "containing," or "involving," and variations thereof, is intended to be broad and encompass the subject matter listed thereafter, equivalents, and additional subject matter not recited, and is not intended to exclude other additives, components, integers or steps. Likewise, the term "comprising" is considered synonymous with the terms "including" or "containing" for applicable legal purposes.

All numerical values in this disclosure are understood as being modified by "about". All singular forms of elements, or any other components described herein including (without limitations) components of the apparatus are understood to include plural forms thereof.

Embodiments of the present invention will now be described, by way of example only, with reference to the accompanying drawings, in which.

Figure 1:
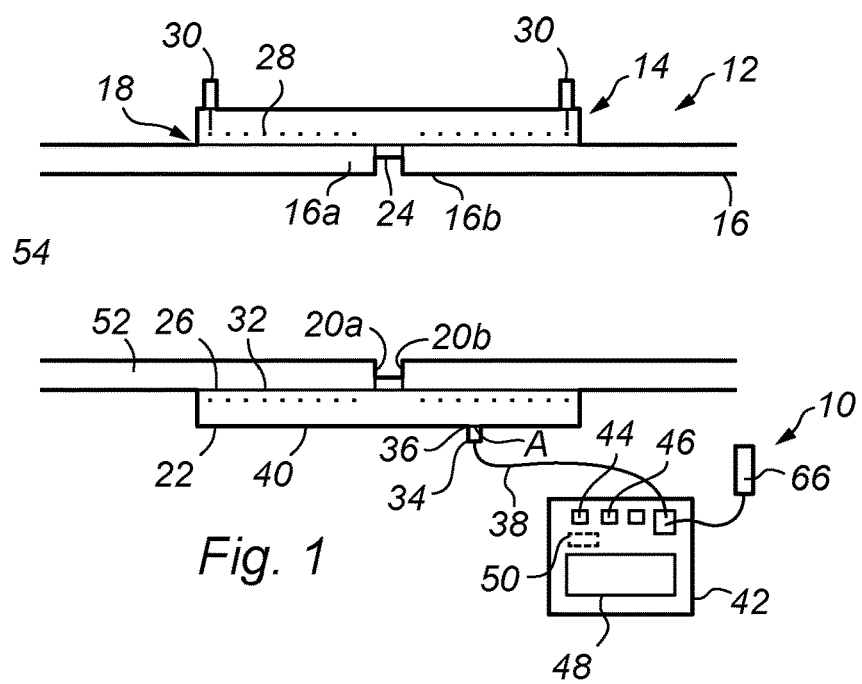
FIG. 1 is a schematic diagram of an ultrasonic non-destructive testing system being used on a plastic pipeline having an electro-fusion weld according to an embodiment of the present invention.

Reference is initially made to FIG. 1 of the drawings which illustrates an ultrasonic non-destructive testing system, generally indicated by reference numeral 10, arranged to perform a defect test 12 on a joint 14, in accordance with an embodiment of the present invention.

In this embodiment joint 14 is formed as an electro-fusion weld 18 between ends of plastic pipe 16 as is known in the art. Typically the plastic pipe 16 tested will be polyethylene which is commonly used in pipes. Two grades of polyethylene are also used, these being PE80 and PE100. However, any plastic may be used including PVC and HDPE. The pipe 16 may have a diameter in the range 25 mm to 1000 mm, with pipes produced in the range 25 mm to 710 mm at present and more typically in the range 25 mm to 180 mm. The pipe 16 can have a wall thickness in the range 3 mm to 63 mm though more typically in the range 4.5 mm to 18 mm.

The joint 14 is provided as an electro-fusion weld 18, though the test may equally be performed on a butt weld or indeed, on any join between two plastics. As is known, an electro-fusion weld 18 is formed by cleaning a first end 20a of a first pipe 16a and a second end 20b of a second pipe 16b, it being desired to join the pipes 16a,16b. The ends 20a,b are inserted into an electro-fusion fitting 22, being a tubular plastic pipe, typically of polyethylene. There is an end stop 24 on the inner surface 26 of the coupling 22 against which the ends 20a,b abut to assist in alignment. The inner diameter of the coupling 22 is selected to match the outer diameter of the pipe 16 to provide a snug fit. The wall thickness of the coupling 22 is typically in the range 3 mm to 63 mm. Embedded in the coupling 22 is a heating wire 28 which is wound around the coupling and extends along it's length. When assembled, a voltage is applied across input terminals 30a,b for a duration equal to the Specified Fusion Time (SFT) and then the joint 14 is allowed to cool. Heating causes the plastic of the fitting 22 to melt and thereby fuse with the plastic of the pipe 16. Sufficient time must be given for the joint to cool following fusion as the welded polymer will re-crystallize and it's ultrasonic properties will change during this process.

Known defects can occur in the welding process. These include defects due to an incorrect heating cycle, surface contamination between the pipe surface 32 and the inner surface 26 of the coupling 22 and misalignment of the pipe ends 20a,b when inserted into the coupling 22.

System 10 comprises a hand held probe 34 which is a single or twin crystal transducer operating at 5 MHz. A diameter of the probe 34 at an end 36 is less than 15 mm. Other frequencies may be used together with other probe dimensions but the probe 34 must be hand-held for placement by a user against a surface 40 of the joint 14. A system 10 may therefore comprise a number of probes 34, the individual probe 34 being selected dependent on the plastic 12 material and dimensions being tested. Ideally the probe 34 will be of a robust design for use in the field. Probe 34 is connected by a cable 38 to a tablet 42. While a cable 38 is described, it will be apparent that a wireless connection could also be used with appropriate electronics mounted in the probe 34.

Tablet 42 acts as the user interface and operating system with inputs 44 and outputs 46. There may be a display 48 to show results and provide a touch sensitive screen for ease of operation by a user. The tablet 42 contains a processor 50 being an analysis module. The tablet 42 also contains a memory so that a record of all the tests can be stored. Tablet 42 may be a laptop or other hand-held device which can be used in the field.

In use, the end 36 of the probe 34 is held against the outer surface 40 of the joint 14, in this case the coupling 22, at a first point A. The probe 34 is arranged to be in contact with, and acoustically coupled to, the outer surface 40 of fitting 22. To assist this water or another coupling agent, may be used. An operator inputs a command signal to the tablet 42 so that the system performs an A-scan at the first point A. A sound signal in the form of a pulse, exits the probe 34 and travels at normal incidence into the surface 40. It travels through the coupling 22 and pipe 16 and is partly reflected at any interface it reaches in the region between the first surface 40 and a back surface 52. Ultimately when it reaches the back surface 52 of the plastic 12 i.e. pipe 16, it will be partly reflected with the remaining pulse travelling into the bore 54 of the pipe 16 which contains air. The reflected signal is collected at the transducer 34 and the A-scan is transmitted to the processor 50 of the tablet 42.

In the region between the first surface 40 and the back surface 52, the sound signal will travel through the fused area. If the plastics of the coupling 22 and the pipe 16 have welded correctly then no interface will exist and no reflection will occur. If fusion has not occurred correctly due to say, over or under heating then an interface will exist and a reflection of the signal will occur. If the sound signal is incident upon the heating wire 28, a lower reflection is observed, due to diffractive scattering. If the sound signal is incident upon a defect such as an air pocket, or a piece of debris such as grease that contaminated the joint, then a greater reflection of the signal will occur.

Figure 2:
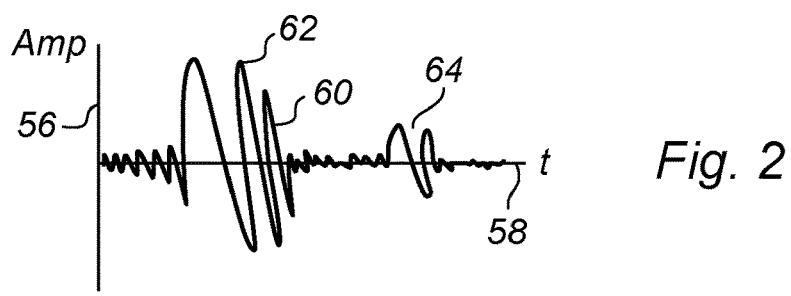
FIG. 2 is a graphical representation of an A-scan carried out by the ultrasound system of FIG. 1 at a first point on the plastic.
Figure 3:
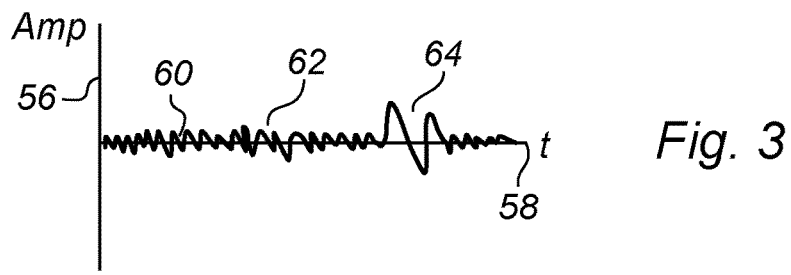
FIG. 3 is a graphical representation of an A-scan carried out by the ultrasound system of FIG. 1 at a second point on the plastic.

Reference is now made to FIGS. 2 and 3 which illustrate A-scans taken at a point on a joint 14 where in FIG. 2, a defect occurs and in FIG. 3, there is no defect and the weld is good. Referring initially to FIG. 2, there is illustrated a graph of amplitude 56 against time 58 for an A-scan trace 60. Trace 60 shows two responses 62,64 in time 58. The later response 64 represents the reflection from the back surface 52. The earlier and greater response 62 is from reflections in the region between the surface 40 and the back surface 52 i.e. the location of the weld. The processor 50 analyses the trace 60 by making a comparison of the two responses 62,64. In a first embodiment the comparison is made by determining a value for peak amplitude in each response 62,64. A ratio of the peak amplitudes is then calculated. A criteria is set for the value of the ratio to determine a level of the result. In this case, the criteria may be that a value of the ratio of the earlier response against the later response indicates a level for the result. Thus, say, a level greater than ten will indicate that a fault has been detected at the point A in the joint 14, whereas a level less than three will indicate that there are no faults or defects in the joint 14 at the point A. Where the level is calculated to be between three and ten, our criteria determines that a definitive result cannot be given. An output 46 of the tablet 42 will indicate the result to the user. This may be by a sound or a light. For a light it may be green for a good weld, red for a bad weld and yellow for an unknown. Alternatively a message may be displayed.

Where an unknown level is displayed a user can decide if this is an indication of a possible fault and choose to treat it as a defect or he may not use the result and repeat the test at the same point or a point close to the original point. If the joint 14 is in say, petroleum gas pipeline, then the criteria and level for a 'good' weld may be set high. In this case, the system 10 may have a binary output indicating only a good or bad weld.

FIG. 2 therefore illustrates an A-scan in which a defect occurs in the joint 14 at the point A. Referring to FIG. 3, the peak amplitude of earlier response 62 is very small compared to the peak amplitude of the later response 64 from the back surface 52 and correspondingly a ratio of less than ten would be calculated. The ratio is therefore indicative of a good weld in the plastic joint 14.

Once a user has received a result for a point A on the plastic joint, they may reposition the probe 34 at another point and repeat the test. Thus any number of points around a joint or weld can be tested.

The A-scan ultrasound system can provide a simple determination of faults in a plastic. The system 10 is compact and portable and is suitable for non-destructive testing and evaluation of pipes outwith the lab environment thus increasing the utility of the system.

In a further embodiment of the system 10, the system 10 is improved by inputting data on the plastic 12 into the processor 50. Referring to FIG. 1, there is shown a barcode scanner 66 which is used to scan barcodes which are located on the pipe 16 and the coupling 22. As pipes and couplings are standard in the industry, the barcode will provide details of the inner and outer diameters and material of the pipe 16. The same information together with the wire diameter, pitch and depth, and taper angle if one exists on the surface 40, can be recorded for the coupling 22. These values are used in the processor to provide a prediction on the time 58 at which each response 62, 64 is expected to appear. If information on the probe 34 is also known, the expected size of the later response 64 may also be predicted. Thus the analysis is improved. While a barcode scanner 66 speeds up the process and removes the possibility of user error, the values could be typed into a suitable user interface on the tablet 42.

Figure 4:
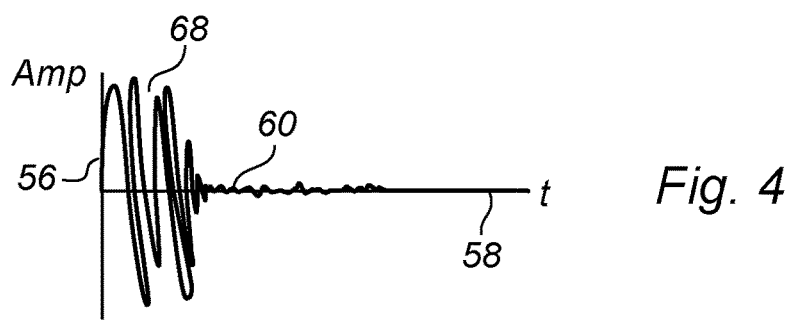
FIG. 4 is a graphical representation of response used to determine coupling efficiency in the ultrasound system of FIG. 1.

In order for a scan of the plastic 12 to be successful, it is important that the transducer 34 is appropriately coupled to the surface 40 of the plastic 12 so that sufficient energy in the signal is passed into the plastic 12. A further embodiment of the present invention provides an electronic coupling system to improve coupling efficiency. In this embodiment a coupling sound signal is output from the transducer 34 and the received signal is used to determine whether coupling is successful. Reference is now made to FIG. 4 of the drawings which illustrates a similar graph to FIGS. 2 and 3, being amplitude 56 against time 58 for a response 68 to the coupling sound signal. The trace 60 now shows an immediate response 68. This response 68 indicates that a majority of the signal is being reflected at the surface 40 and therefore very little is being input to the plastic. The coupling efficiency is therefore not acceptable. A red light or sound may be output from the tablet 42 to indicate this condition to a user. A user would then adjust the probe 34 position, clean the probe end 36 and the surface 40 at point A or add more coupling agent, such as water, at the contact point. Further coupling signals would be transmitted until the ring down time of response 68 was at a minimum to indicate a high coupling efficiency. This result is indicated to the user by say, a green light or a change in sound.

In this embodiment, the amplitude of the received signal response 68 is used to determine efficient coupling. Alternatively the received signal response may be compared to a known received coupling signal achieved on the joint under lab conditions. This apriori knowledge of the expected response may be input to the processor as a look-up database. Also coupling efficiency could be determined from a reflection from an interface in the joint, a reflection from the back surface, an amount of energy reflected or the time taken for a reflection to reach the transducer.

In an embodiment, a feedback system on efficient coupling is included. Here the indication of coupling is displayed to the user, so that they get feedback on the efficiency of coupling and are therefore prompted to adjust the probe position accordingly to obtain the most efficient coupling. A sequence of lights are used with a first light indicating that the probe has been placed on something similar to a fitting (i.e. energy is being transmitted) and a final light indicating that the front portion of the response signal is similar to a profile that we would expect from a fitting of the type that the system has been told that it is testing (e.g. an electrofusion fitting). As the second step can be difficult to obtain due to bad alignment as the operator may be trying to test the underside of a fitting down a trench, for example, a series of lights between the first and final can be used to assist in indicating to an operator getting to the final light position by adjusting the alignment of the probe.

In a yet further embodiment, the system includes an electronic performance system which is used to determine that an A-scan can be performed on the plastic. In this embodiment an operating sound signal is input to the plastic at the point A. The received signal response is analysed to determine that sufficient energy has been received at a location through the joint to analyse and provide a result. Where efficiency coupling and performance are included in a single system 10, the coupling efficiency will be undertaken first. An alternative analysis method for determining performance may be in analysing the amplitude of the response 64 from the back surface and ensuring that this is sufficient for calculations. An output in the form of lights and/or sounds from the tablet 42 will indicate to the user that the performance criteria has been met and the system 10 is ready to perform an A-scan on the plastic 12.

By determining coupling efficiency and performance a reliable test result will be achieved. This allows unskilled operators such as pipe laying technicians to perform a test.

In addition to the barcode scanner 66 other additional features may be incorporated in the system. A GPS recorder will allow mapping on points along a pipeline that are being tested. Further a probe inclination and position detector can be included so as to record the position and orientation of the probe on a pipe joint.

Additionally, the processor can be programmed to provide different comparison techniques on the responses. Comparison of reflected energy levels, area of response on the trace, amplitude, frequency, pulse width, phase or features could be used. Modelled responses or those collected in standard joints in the laboratory can be used for comparison. Further methods may be to improved modelling using finite element and analytical techniques to 'model' the system, thereby trying to predict what the interface response would be; signal processing in analysing the acquired signal in the time and frequency domain (including wavelets) to detect variability from a predetermined expected response; and, automatic defect recognition from the information gathered in signal processing, using pattern recognition techniques such as fuzzy logic, probabilistic methods, neural networks etc. to make an evaluation of the quality of the weld and the nature of the defect.

The principle advantage of the present invention is that it provides a non-destructive testing system and method of testing joints in plastic pipes using an ultrasonic A-scan which can thereby be provided in a hand-held device and is simple to operate.

A further advantage of the present invention is that it provides a non-destructive testing system and method of testing joints in plastic pipes which provides result indicative of the quality of the weld in a form which allows pipe laying technicians to perform tests in the field.

It will be appreciated to those skilled in the art that various modifications may be made to the invention herein described without departing from the scope thereof. For example, while a standard electro-fusion pipe joint between two plastic pipes has been described the method is applicable to all types of plastic pipe fittings such as Tapping T's, reducers and elbows.

The invention claimed is:

1. A method of non-destructive testing of a joint in plastic pipes, comprising:
    locating a hand-held ultrasonic transducer at a first point on an outer surface of the joint and performing an A-scan through the joint between the outer surface of the joint and a back surface of the joint at the first point;
    detecting a trace of the A-scan and identifying an interface response representing one or more reflections of a sound signal from one or more surfaces in a region between the outer surface of the coupling sleeve and the back surface;
    identifying a back surface response in the A-scan representing one or more reflections of the sound signal from the back surface;
    comparing a first peak amplitude of the interface response with a second peak amplitude of the back surface response to provide a result; and
    outputting the result, the result being indicative of a quality of the joint.

2. A method according to claim 1 wherein the method comprises the step of determining effective coupling between the joint and the ultrasonic transducer by analysis of a coupling response.

3. A method according to claim 2 wherein the coupling response is indicative of a reflection from the outer surface.

4. A method according to claim 2 wherein a scaled output is given being indicative of the efficiency of the coupling between the joint and the ultrasonic transducer.

5. A method according to claim 1 wherein the comparison provides a ratio and wherein the ratio is used to determine the result.

6. A method according to claim 5 wherein the result is a binary output of two levels indicative of whether or not a defect exists in the joint.

7. A method according to claim 1 wherein the result is a level on a scale.

8. A method according to claim 1 wherein the comparison is to an energy of the sound signal at the transducer.

9. A method according to claim 1 wherein the comparison is to a second trace.

10. A method according to claim 9 wherein the second trace is a reference trace from an A-scan taken on an identical joint without defects.

11. A method according to claim 9 wherein the second trace is generated from a simulated model of the joint.

12. A method according to claim 1, wherein the comparison determines a ratio between the first peak amplitude from the interface response and the second peak amplitude from the back surface response.

13. A method according to claim 1 wherein the step of performing the A-scan is on a butt weld at the joint.

14. A method according to claim 1 wherein the step of performing the A-scan is on an electro-fusion weld at the joint.

15. A method according to claim 1 wherein the method comprises the step of inputting data relating to the joint before the A-scan on the joint is performed.

16. A method according to claim 15 wherein the step of inputting data relating to the joint is by scanning a bar code on the joint, the barcode containing data on the joint.

17. A method according to claim 1 wherein the method comprises the step of determining that an A-scan can be performed on the joint by analysing a response created by a reflection of a sound signal from an interface after the outer surface.

18. An ultrasonic non-destructive testing system for a joint in plastic pipes, the system comprising:
    a hand-held ultrasonic transducer, the transducer being located at a first point on an outer surface of the joint and operable to perform an A-scan of the joint between the outer surface and a back surface of the joint at the first point; and
    an operating unit, the operating unit including:
        a user interface with one or more inputs for a user to control the system and one or more outputs to display a result of the system; and
        an analysis module for receiving the A-scan, detecting the presence of an interface response representing one or more reflections of the sound signal from an interface in a region of the joint between the outer surface and the back surface, detecting the presence of a back surface response representing one or more reflections of the sound signal from the back surface, performing a comparison of a first peak amplitude of the interface response to a second peak amplitude of the back surface signal, and determining the result based on the comparison, wherein the result is outputted by the one or more outputs from the user interface.

* * * * *